US00PP34201P2

(12) United States Plant Patent
Michael

(10) Patent No.: US PP34,201 P2
(45) Date of Patent: May 3, 2022

(54) ***XSEMPONIUM* PLANT NAMED 'SIENNA'**

(50) Latin Name: **x *Semponium***
Varietal Denomination: Sienna

(71) Applicant: Surreal Succulents, Cornwall (GB)

(72) Inventor: Daniel Michael, Cornwall (GB)

(73) Assignee: Belgicactus B.V.B.A., Westerlo (BE)

( * ) Notice: Subject to any disclaimer, the term of this patent is extended or adjusted under 35 U.S.C. 154(b) by 0 days.

(21) Appl. No.: 17/208,229

(22) Filed: Mar. 22, 2021

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./263.1, 373
CPC ..... A01H 5/12; A01H 5/02; A01H 5/00
See application file for complete search history.

(56) References Cited

PUBLICATIONS https://www.researchgate.net/publication/344725671_Semponium_un_nuovo_ibrido_intergenerico_nella_famiglia_delle_Crassulaceae_Piante_Grasse_402_2020_78-81; Oct. 2020; 7 pages.*

* cited by examiner

*Primary Examiner* — Kent L Bell
(74) *Attorney, Agent, or Firm* — Penny J. Aguirre

(57) ABSTRACT

A new cultivar of x *Semponium* plant named 'Sienna' that is characterized by its compact, dense growth habit with short stems, its uniformly neat, conical growth habit, its tightly compact rings of adjacent foliage rosettes in tiers from the main stem, its production of multiple offsets; 1 head produces an average of 12 offsets, and its unique foliage coloration: in winter to early spring; green with dark purple-brown margins and light green centers, in mid spring; purple-brown, in late spring to autumn; bright orange with light green centers.

2 Drawing Sheets

Botanical classification: x *Semponium.*
Variety denomination: 'Sienna'.

CROSS REFERENCE TO A RELATED APPLICATION

This application is related to a European plant breeders' rights application filed on Mar. 11, 2021, application No. 2021/0764. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of x *Semponium*, an *interspecific* hybrid plant and referred to hereinafter by its cultivar name, 'Sienna'. The new cultivar of x *Semponium* is a frost hardy succulent subshrub perennial grown for ornamental foliage use in landscapes and containers.

The new cultivar arose from an ongoing breeding program by the Inventor in Penzance, Cornwall, United Kingdom. The goal of the breeding program was to produce a new cultivar of x *Semponium* with unique foliage coloration, a compact growth habit, a dense and neat plant habit with production of many side shoots.

The new cultivar arose from a cross made by the Inventor in 2016 between *Aeonium* 'Ice Warrior' (not patented) as the female parent and *Sempervivum ciliosum* 'Green Ice' (not patented) as the male parent. The Inventor selected 'Sienna' as a single unique plant amongst the seedlings that resulted from the above cross in 2018.

Asexual propagation of the new cultivar was first accomplished by the Inventor by stem root cuttings in 2018 in Penzance, Cornwall, United Kingdom. Asexual propagation by cuttings and offshoots has determined the characteristics to be stable and reproduced true to type in successive generations.

SUMMARY OF THE INVENTION

The following traits have been repeatedly observed and are determined to be the characteristics of the new cultivar. These attributes in combination distinguish 'Sienna' as a unique cultivar of x *Semponium.*

1. 'Sienna' exhibits a compact, dense growth habit with short stems.
2. 'Sienna' exhibits a uniformly neat, conical growth habit.
3. 'Sienna' exhibits tightly compact rings of adjacent foliage rosettes in tiers from the main stem.
4. 'Sienna' exhibits production of multiple offsets; 1 head produces an average of 12 offsets.
5. 'Sienna' exhibits unique foliage coloration: in winter to early spring; green with dark purple-brown margins and light green centers, in mid spring; purple-brown, in late spring to autumn; bright orange with light green centers.

The female parent plant differs from 'Sienna' in having taller stems, fewer offsets, rosettes that are larger in size, plant habit that is less dense and compact, leaves that are larger in size, and foliage that is green with purple-red margins from spring to autumn. The male parent plant differs from 'Sienna' in having foliage that is green in color with hairs on both surfaces, and rosettes and leaves that are smaller in size. 'Sienna' can be most closely compared to the x *Semponium* cultivars 'Destiny' (not patented) and 'Diamond' (not patented). 'Destiny' differs from 'Sienna' in having leaves that are larger in size, spade-shaped, and very dark maroon in color with the lower surface becoming light green towards the base with numerous red spots. 'Diamond' differs from 'Sienna' in having leaves that are larger in size and pale green in color with a few scattered spots.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Surreal Succulents, Researchgate, and National Gardening Association.

BRIEF DESCRIPTION OF THE DRAWINGS

The accompanying color photographs illustrate the overall appearance and distinct characteristics of 3-year-old plants of 'Sienna' as grown outdoors in a 5-liter container in Penzance, Cornwall, United Kingdom.

The photograph in FIG. 1 provides a side view of a plant of 'Sienna' in summer.

Figure 1:
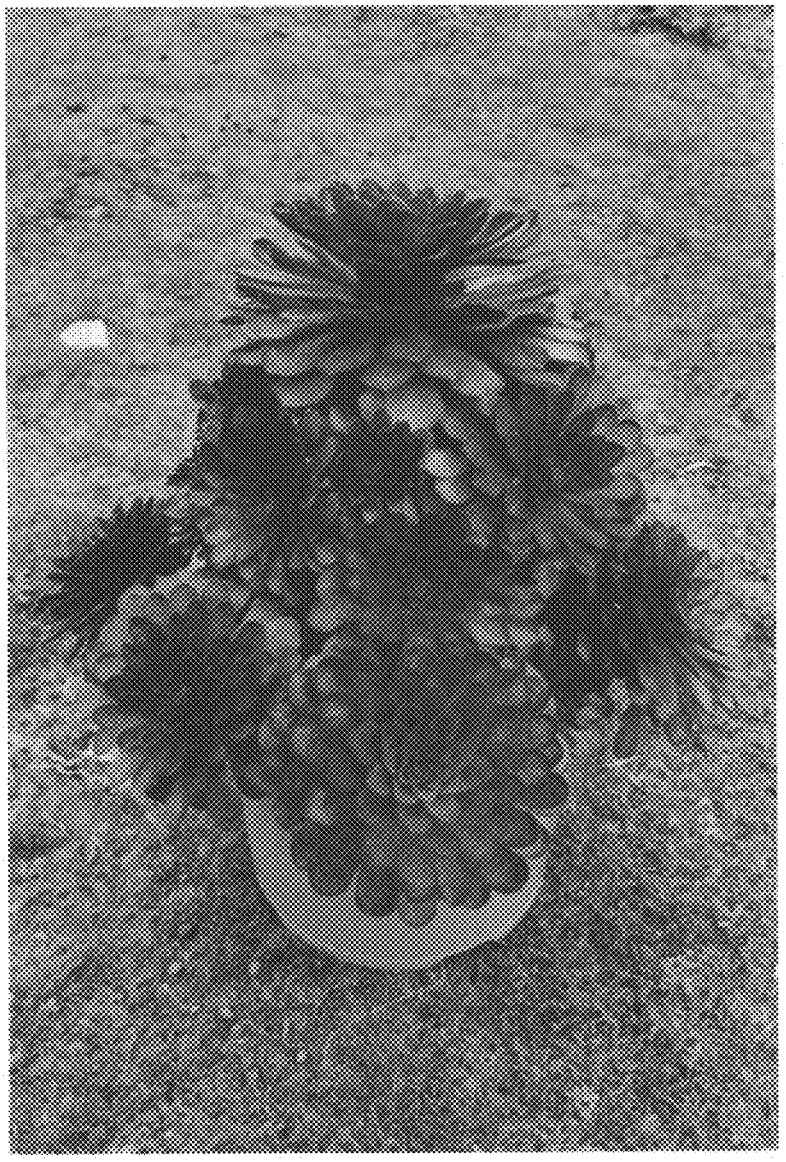
Figure 2:
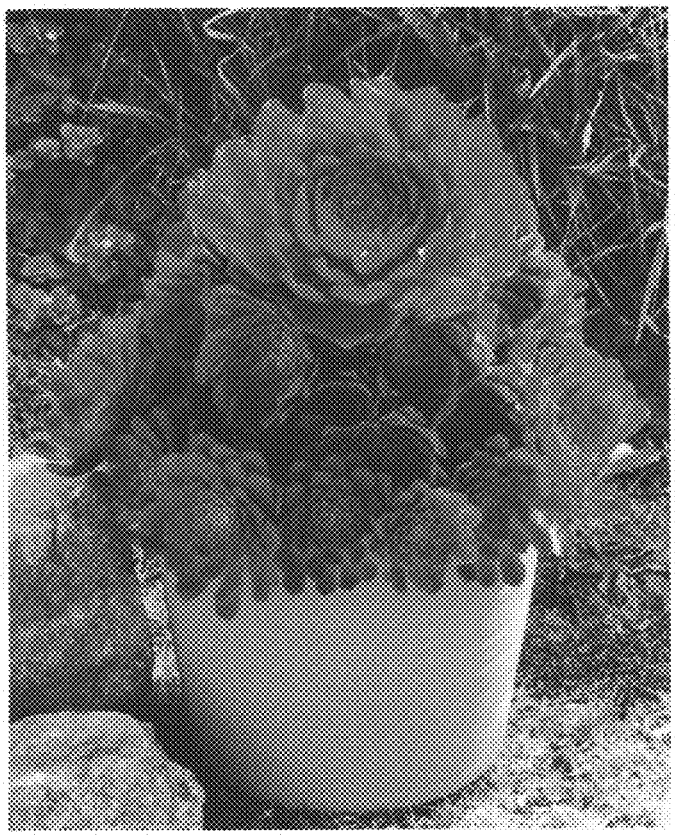
Figure 3:
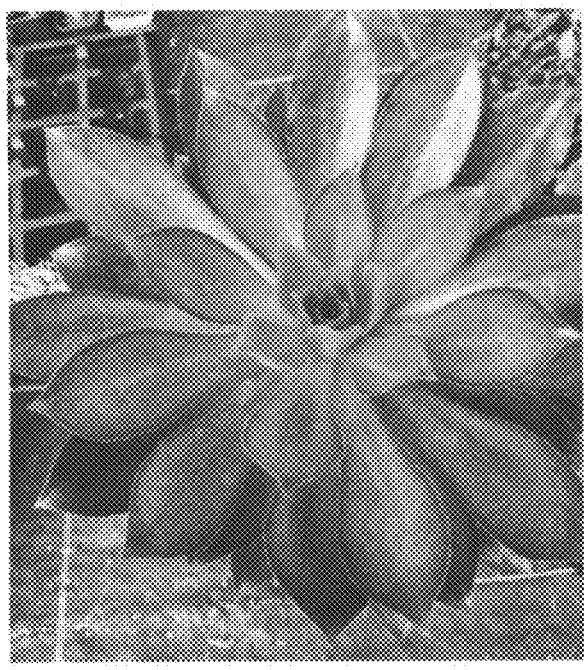

The photograph in FIG. 2 provides a close-up view of a rosette of 'Sienna' in winter to early spring.

The colors in the photographs may differ slightly from the color values cited in the detailed botanical description, which accurately describe the colors of the new x *Semponium*.

DETAILED BOTANICAL DESCRIPTION

The following is a detailed description of the new cultivar as observed on 3-year-old plants of 'Sierra' as grown outdoors (April to October) and in an unheated polytunnel (November to March) in 5-liter containers in Penzance, Cornwall, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen succulent perennial.

*Plant shape.*—Conical.

*Plant habit.*—Compact, dense basal rosette with offsets clustered around main rosette.

*Height and spread.*—Reaches up to 40 cm in height and width.

*Hardiness.*—At least hardy to −5° C., has not been tested in colder climates.

*Diseases and pests.*—No susceptibility or resistance to diseases or pests has been observed.

*Root description.*—Fibrous.

*Propagation.*—Stem cuttings.

*Root development.*—Roots initiate in an average of 6 weeks and fully root as a young plant in a P7 container in about 2 months.

*Growth rate.*—Moderate.

Stem description:

*Stem shape.*—Cylindrical.

*Stem size.*—1 to 3 cm in width and up to 32 cm in length.

*Stem surface.*—Smooth with leaf scars at the base.

*Stem arrangement.*—Verticillate, whorled in concentric rings of lateral branches.

*Stem aspect.*—Horizontal to vertical.

*Internode length.*—Up to 6 cm.

*Stem color.*—198B.

Foliage description:

*Leaf shape.*—Narrowly spathulate.

*Leaf division.*—Simple.

*Leaf arrangement.*—Rosette.

*Leaf quantity.*—Average of 80 to 100 per rosette.

*Leaf base.*—Narrowly cuneate.

*Leaf apex.*—Blunt round, mucronate.

*Leaf venation.*—No veins visible.

*Leaf margins.*—Ciliate.

*Leaf attachment.*—Sessile.

*Leaf orientation.*—Flat to slightly concave.

*Leaf substance.*—Succulent.

*Leaf thickness.*—1.5 to 2 mm.

*Leaf surface.*—Upper and lower surface smooth and waxy with ciliate margins.

*Leaf color* (*upper and lower surface*).—In winter to early spring; 145B to 145C with margins 183B and maturing leaves suffused with N77A, in mid spring; mature spring and to early autumn; 183A with centers 137B, in late spring to autumn; a blend of 170A and 171A with centers 137B.

*Leaf size.*—Average of 7.5 cm in length and 2 cm in width.

*Rosette size.*—Apical; 26 cm in width with 80 to 100 leaves, lateral; 17 cm in width with 60 to 80 leaves.

Flower description: No flowers have been observed to date.

It is claimed:

1. A new and distinct variety of x *Semponium* plant named 'Sienna' as described and illustrated herein.

* * * * *